US00PP22062P3

(12) United States Plant Patent
de Teresa Cortes

(10) Patent No.: US PP22,062 P3
(45) Date of Patent: Aug. 9, 2011

(54) MANDARIN TREE NAMED 'MANDARIN QUEEN'

(50) Latin Name: *Citrus reticulata*
Varietal Denomination: Mandarin Queen

(75) Inventor: Emilio de Teresa Cortes, El Puig (ES)

(73) Assignee: Angel Teresa Hermanos, S.A., Alicante (ES)

( * ) Notice: Subject to any disclaimer, the term of this patent is extended or adjusted under 35 U.S.C. 154(b) by 0 days.

(21) Appl. No.: 12/584,258

(22) Filed: Sep. 1, 2009

(65) Prior Publication Data

US 2011/0055988 P1 Mar. 3, 2011

(51) Int. Cl.
*A01H 5/00* (2006.01)

(52) U.S. Cl. ..... Plt./202

(58) Field of Classification Search ..... Plt./202, Plt./201
See application file for complete search history.

(56) References Cited

OTHER PUBLICATIONS

Hutchison. Performance of 'Queen' Orange Trees on 15 Citrus Rootstocks. Proc. Fla. State Hort. Soc. 94:29-30, 1981.*
Upov-rom GTITM Plant Variet Database 2010/03, GTI Jouve Retrieval Software, Citation for Citrus 'Queen', 2 pages.*

* cited by examiner

*Primary Examiner* — June Hwu
(74) *Attorney, Agent, or Firm* — Kilpatrick Townsend & Stockton LLP

(57) ABSTRACT

'Mandarin Queen' is a new and distinctive mandarin hybrid cultivar, which distinguishes itself by having mid to late season maturity, a large size, distinguished flat shape, easily peeled, a smooth rind texture, white albedo, red color, rich sweet flavor and pleasant aroma. It further distinguishes itself by being seedless or virtually seedless.

9 Drawing Sheets

Latin name of the genus and species: The mandarin cultivar of this invention is botanically identified as *Citrus reticulata.*

Variety denomination: The variety denomination is 'Mandarin Queen'.

BACKGROUND OF THE INVENTION

This invention relates to a new and distinctive mandarin hybrid cultivar designated 'Queen' which was developed in Spain. It is distinguished from other cultivars by producing fruit that combines mid to late season maturity, large size, distinguished flat shape, easily peeled, smooth rind texture, white albedo, red color, rich sweet flavor and pleasant aroma. It further distinguishes itself by being seedless or virtually seedless.

BRIEF SUMMARY OF THE INVENTION

'Mandarin Queen' mandarin appeared in Pilar de la Horadada, Alicante, Spain in 1987 as a natural hybrid of a 'Satsuma' mandarin seed parent and an unknown pollen parent. First, seeds of the 'Satsuma' fruit were planted and one of the planted seeds produced a tree having different fruit. The tree from this planted seed was then grafted over 'Macrophylla', 'Volkameriana', 'Carrizo' and 'Cleopatra' rootstocks. Fruit production and evaluation began in 1995. Trials with cross pollination have been made with 'Orogrande', 'Oronules', 'Ortanique', 'Clemenpons,' 'Fortune' and 'Valencia-Late'. Only the trials with 'Fortune' have occasionally produced some seed in the fruit of the 'Mandarin Queen' mandarin.

In 2006, budwood was sent to a center in Valencia, Spain, to clean the variety of the tristeza virus. The budwood was grafted to rootstock in Alicante, Spain, thereby asexually reproducing the new variety. In 2007, four trees certified as tristeza-free were kept in a breeding block of the center for further propagation and four trees were sent to a breeding block in Pilar de la Horadada, Alicante, Spain. Fruit production of those trees commenced in 2009.

BRIEF DESCRIPTION OF THE DRAWINGS

The figures depict various characteristics of 'Mandarin Queen'.

DETAILED DESCRIPTION OF THE INVENTION

The following is a detailed description of the new *Citrus reticulata*, 'Mandarin Queen', based upon observation of four year old plants grown in Alicante, Spain. The color designations being according to The R.H.S. Colour Chart published by The Royal Horticultural Society of London, England. Further, additional character descriptions listed herein are in accordance with the *IPGRI Descriptors for Citrus*.

Figure 3A:
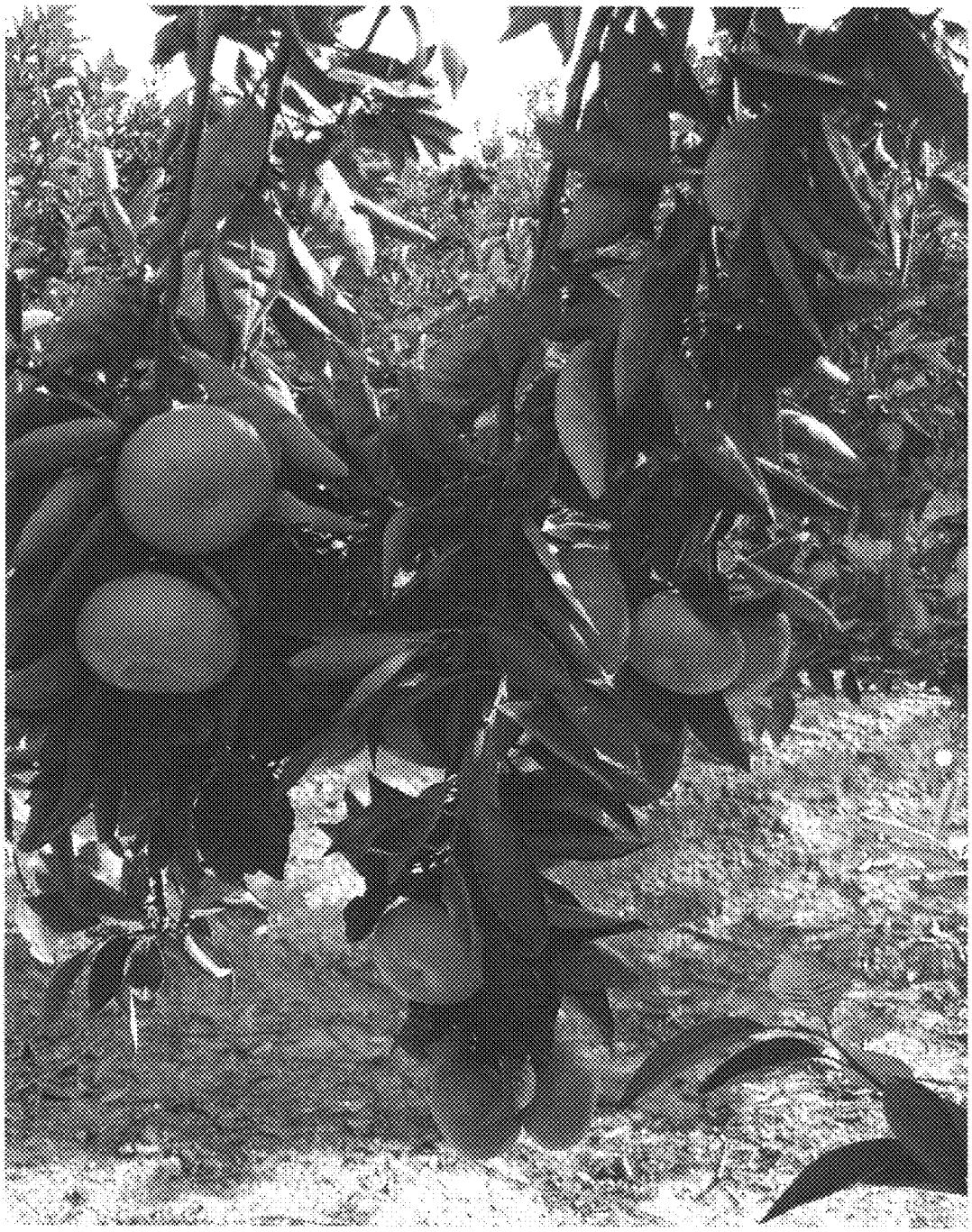
FIG. 3A shows the fruit of a three year old 'Queen' tree in week three, grafted over a 20 year old Cleopatra rootstock with Valencia Late.
Figure 3B:
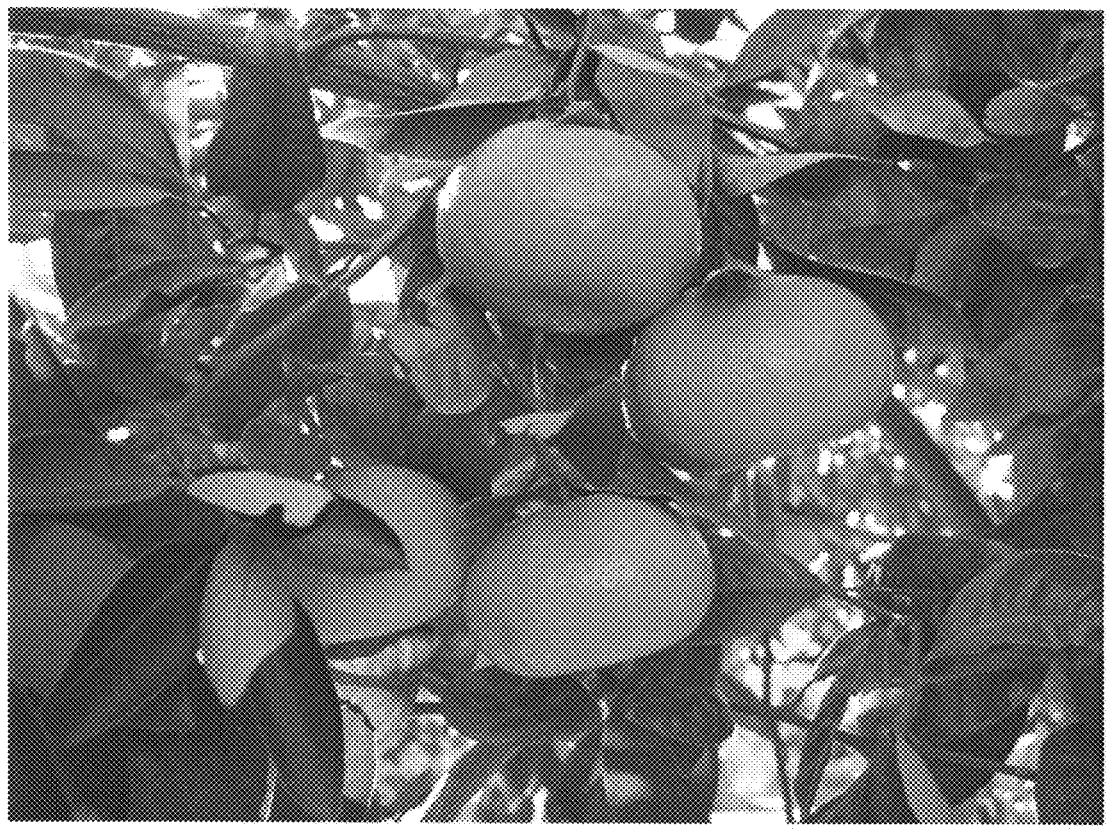
FIG. 3B shows a close-up view of the fruit of Queen in week three.

Fruit of 'Queen' mandarins are virtually seedless and do not cross-pollinate with other mandarins as it is auto incompatible. 'Queen' mandarin is a mid to late season variety, harvested between the beginning of January to the end of April in Pilar de la Horadada, Alicante, Spain. The fruit is very easy to peel, with a flat shape and having a diameter between 58-68 mm. The fruit has around 49% juice content, is very homogeneous, and has a red fruit skin color (see FIG. 3A), with a typical flat shape (see FIG. 3B). The oil glands have a pleasant aroma. At maturity the 'Queen' mandarin fruit has around 1.05% of acid concentration and 12° Brix. At the beginning of January, the 'Queen' mandarin has around 1.25% of acid concentration and 11.5° Brix over Macrophylla rootstock. By the end of February, the 'Queen' mandarin has around 1.15% of acid concentration and 13.5° Brix over Cleopatra rootstock. By mid-April, the 'Queen' mandarin has around 1.00% of acid concentration and 15° Brix over Cleopatra rootstock.

Figure 4A:
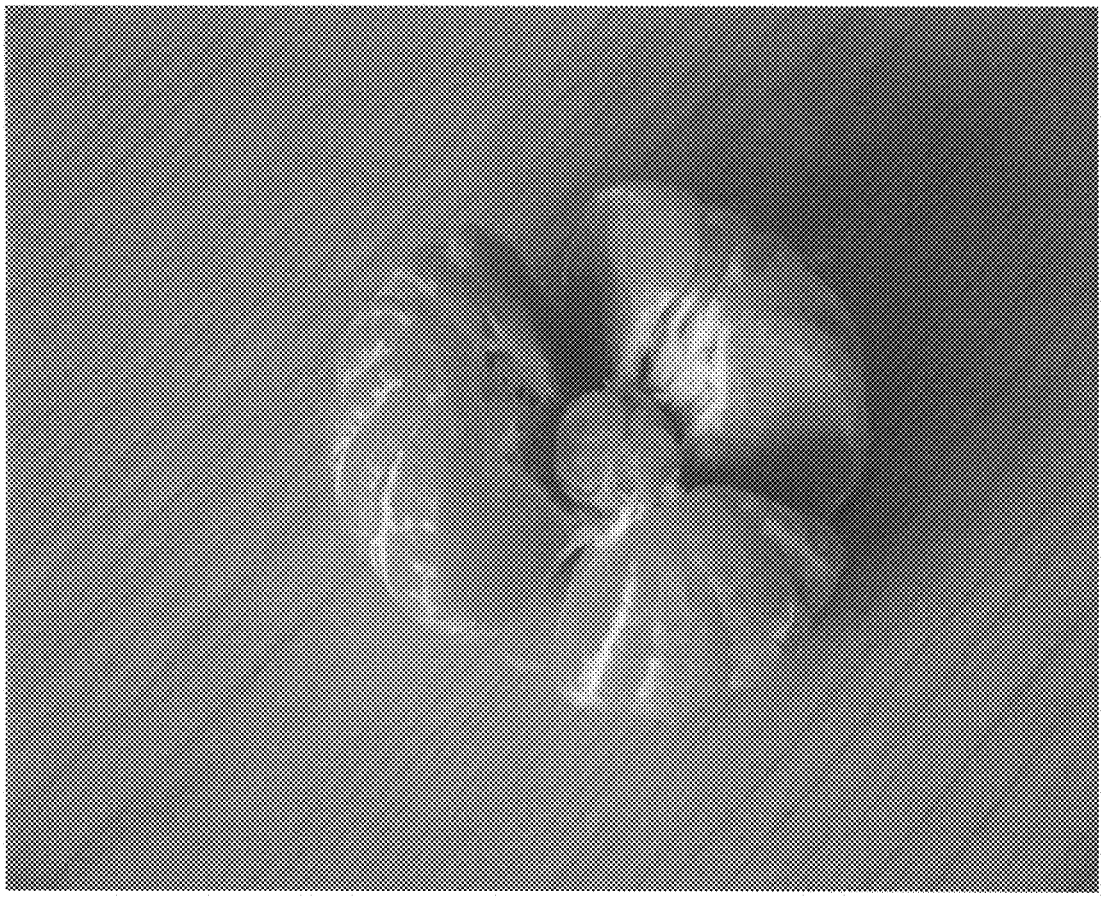
FIG. 4A shows the peeled fruit of 'Queen' mandarin with navel.

The flavor is sweet and lightly acidic. The pulp has a smooth texture and the segments have an easy-eating texture. Some 'Queen' fruit have navels that differ from 1 to 5 mm in diameter and develop inside as a typical navel orange does (See FIG. 4A). Usually, between 14 and 16 segments are found in a 'Queen' mandarin fruit. Growing conditions are easy to manage as they do not need pruning and treatments to produce a good yield.

Comparison With Existing Mandarins

The 'Mandarin Queen' mandarin variety differs from its parents in harvesting period. 'Satsuma' is harvested in October through December and 'Mandarin Queen' is harvested in January through April, in Pilar de la Horadada, Alicante, Spain. 'Satsuma' has a puffy skin, while 'Mandarin Queen' has a skin that is easy to peel, but not puffy. 'Satsuma' has an orange color, while 'Mandarin Queen' has a vivid reddish orange color. 'Satsuma' has low level acidity during harvesting period, between 0.90 and 0.60, while 'Mandarin Queen' has an acid level of 1.25 and 1.00 during harvesting.

'Mandarin Queen' mandarin differs from main mid to late season cultivars because trees of 'Mandarin Queen' do not show alternate bearing and do not need to be pruned as, for example, 'Orri' or 'Nadorcott'. 'Mandarin Queen' is virtually seedless, larger sized and a deeper red color than 'Orri' and 'Nadorcott'. 'Mandarin Queen' mandarin's resistance to heat and cold is similar to 'Clementine'.

Trees, Foliage and Flowers

Figure 5:
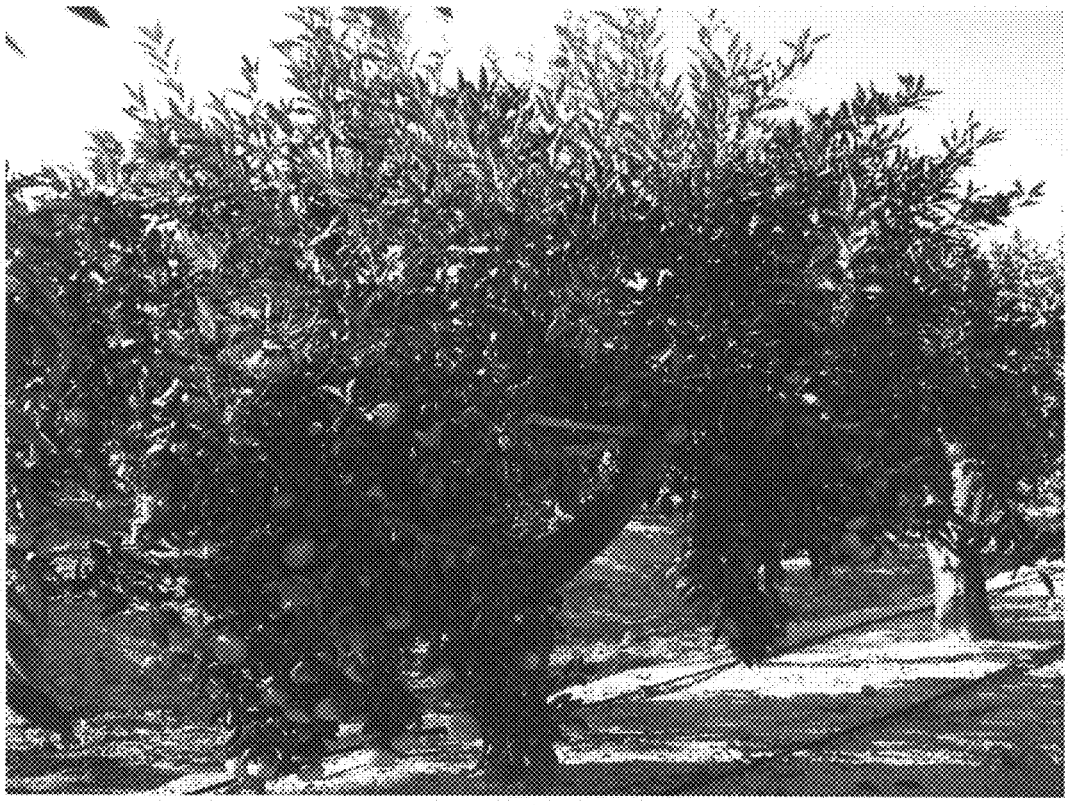
FIG. 5 shows a view of a three year old grafted 'Mandarin Queen' mandarin tree over a 20 year old rootstock of 'Cleopatra' (Valencia Late).
Figure 6:
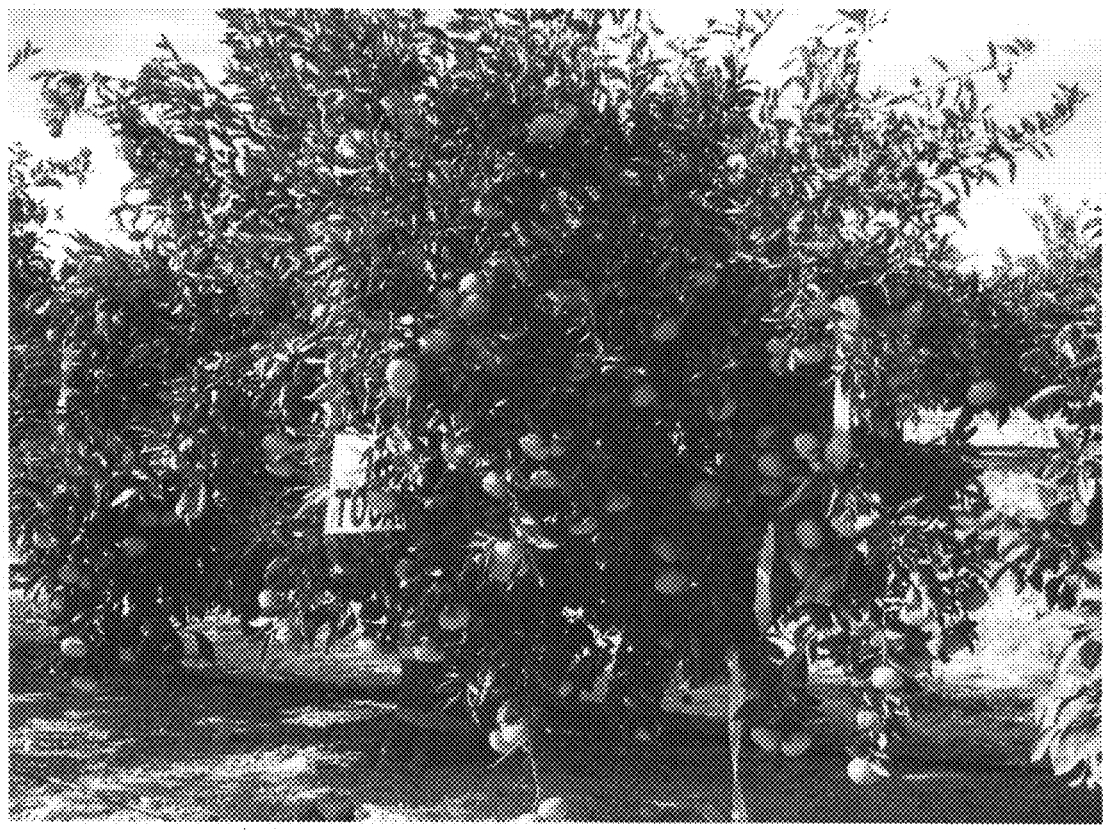
FIG. 6 shows a four year old grafted 'Mandarin Queen' mandarin tree over a 20 year old rootstock of 'Cleopatra' (Valencia Late).
Figure 7:
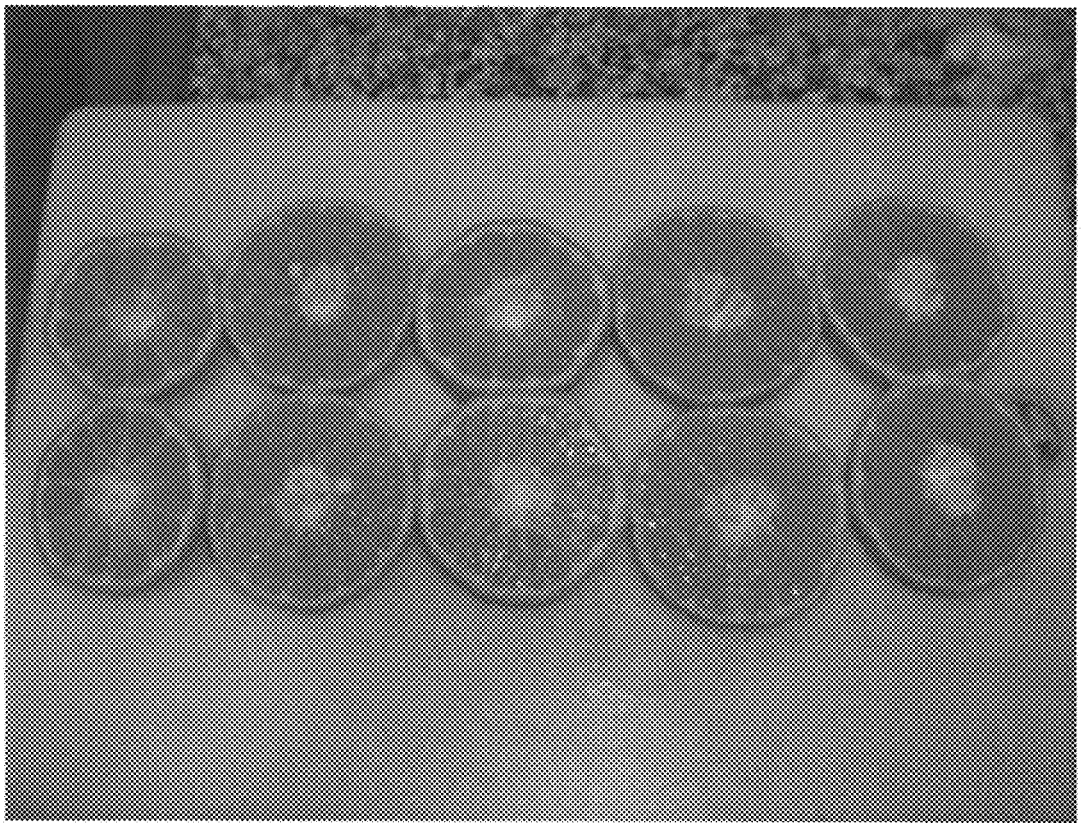
FIG. 7 shows a cross section of representative mid-season 'Queen' fruit.
Figure 8A:
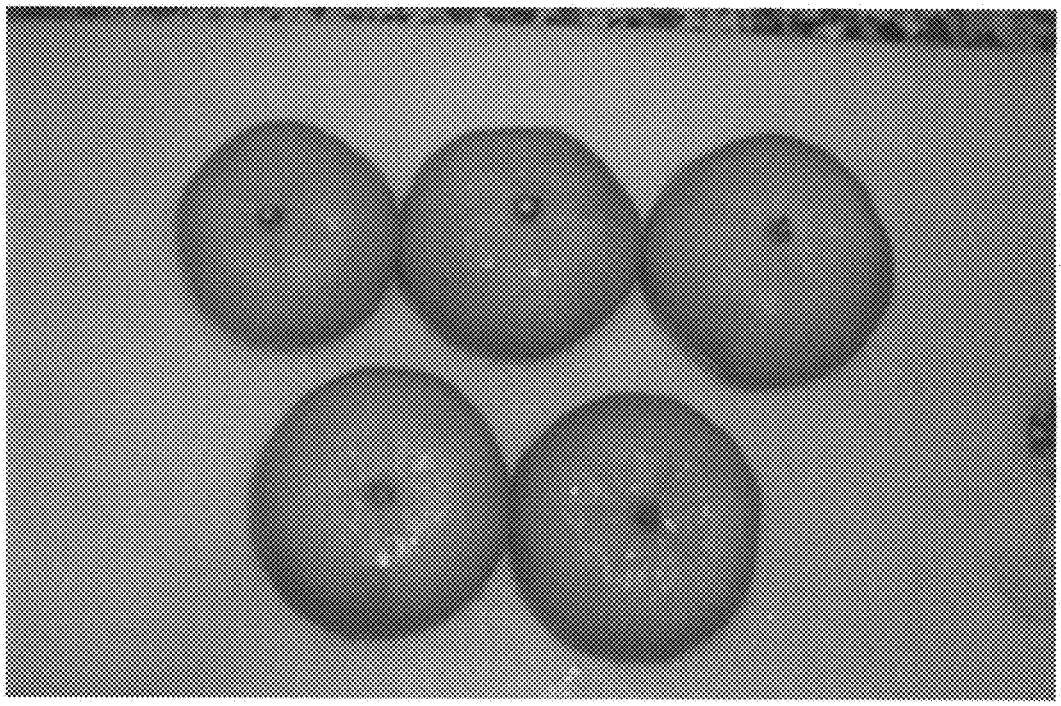
FIG. 8A shows a top view (stem end) of a typical fruit of 'Queen'.
Figure 8B:
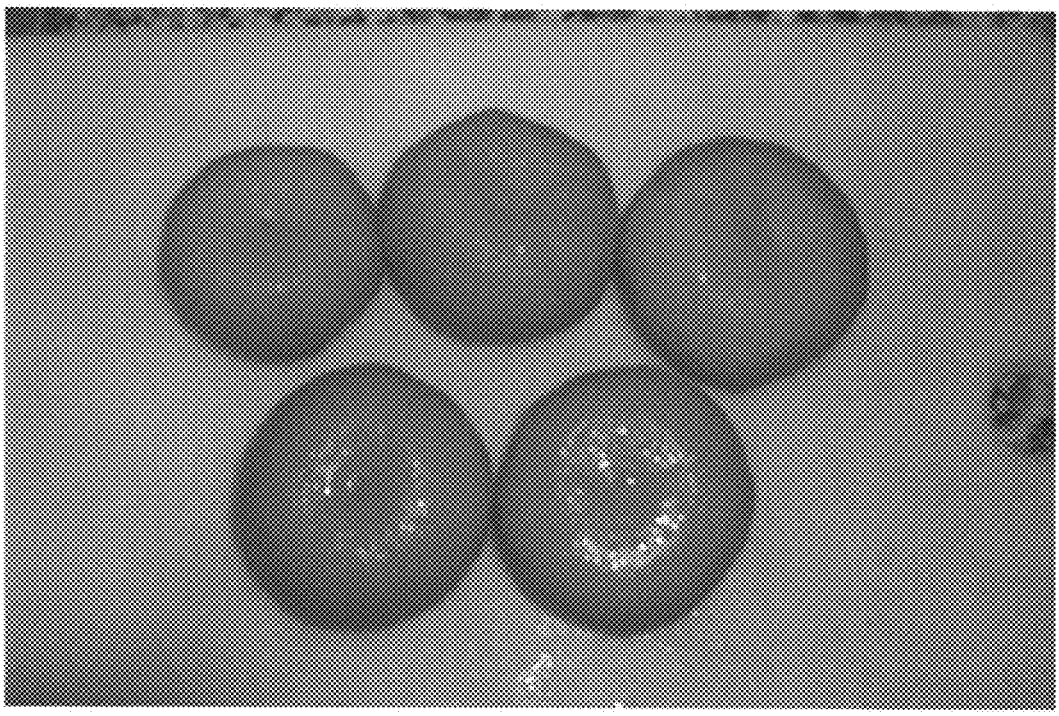
FIG. 8B shows a bottom view (blossom end or tip) of a typical fruit of 'Queen'.

The 'Mandarin Queen' mandarin tree has a drooping growth habit, obloid shape and is without spines. The bark of the trunk has a green and brown color (RHS color: 199 A) and the branches tend to curve down. The surface texture of the trunk is even. The tree is vigorous with dark green leaves (See FIGS. 5-6). A typical five-year old 'Mandarin Queen' mandarin tree has an average height of 2.60 m and an average width of 2.20 m. A typical truck diameter is 7 cm at 30 cm about the ground.

Figure 1:
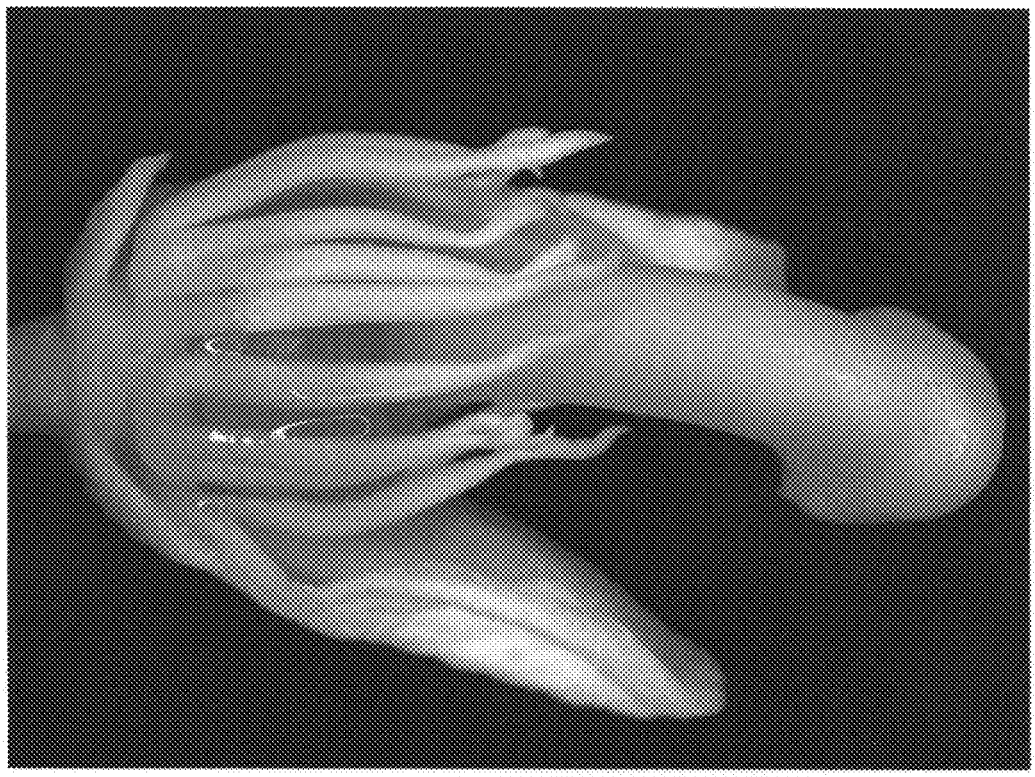
FIG. 1 shows the 'Mandarin Queen' mandarin flower.
Figure 2:
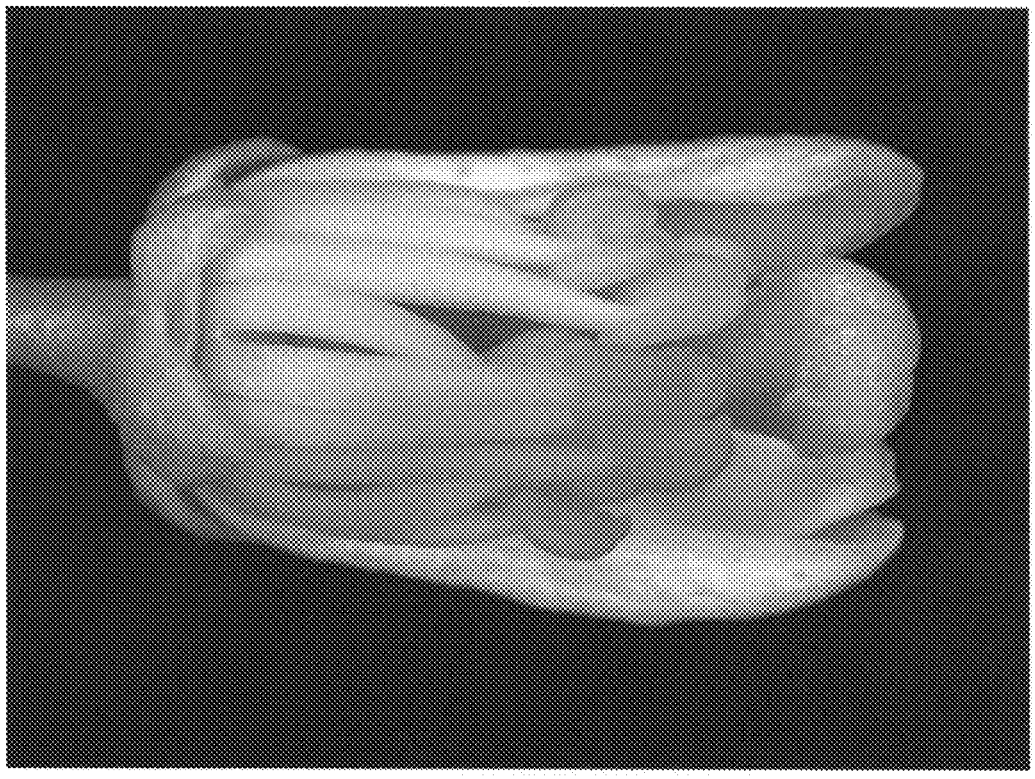
FIG. 2 shows the 'Fortune' mandarin flower.
Figure 4B:
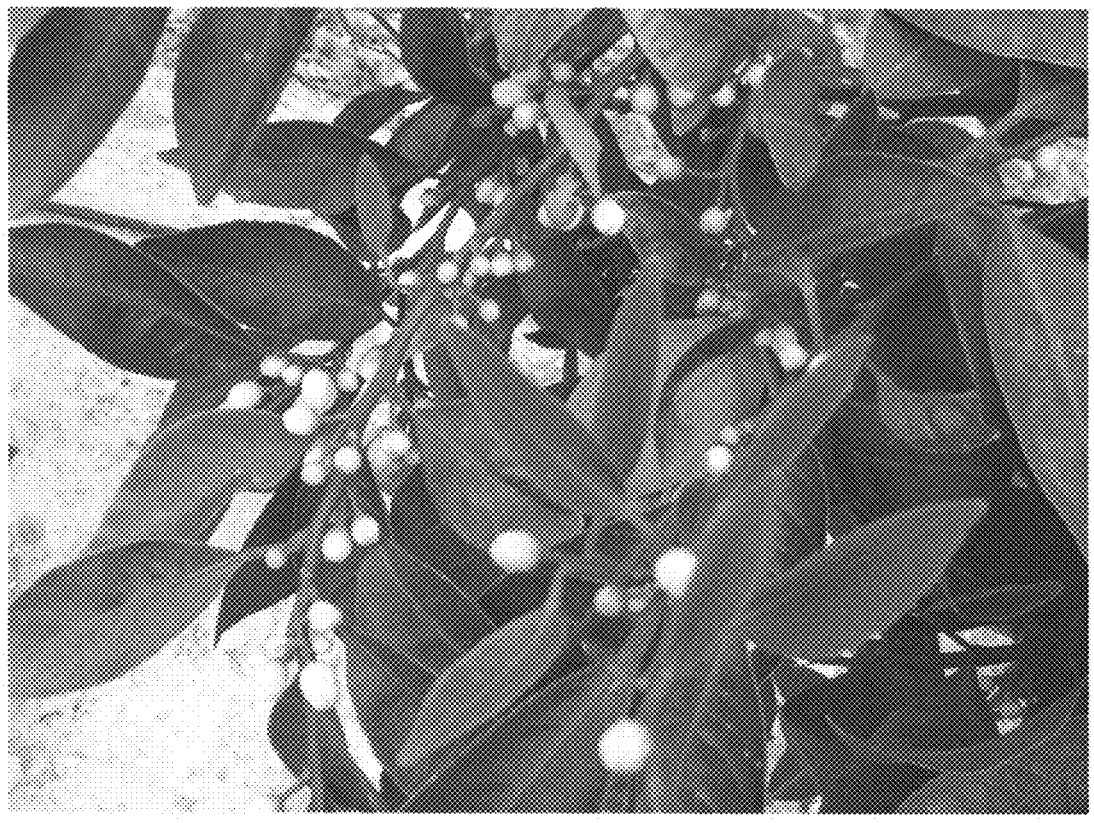
FIG. 4B shows the flower buds and flowers.

Flowering occurs at the end of March to April in Pilar de la Horadada, Alicante, Spain (See, FIG. 4B) The flowers have no pollen and are hermaphrodite. Open flowers are white (RHS color: 155 C) and have five petals. The flowers do not have anthers and cannot produce pollen (See, FIGS. 1, 2). The ratio of petal length and width, and stamen length, is medium. The average size of the flower is 8 to 13 mm and the average number of stamens is 16 to 20. The average number of pistil per flower is 1, and the average length of pistils is 15 to 20 mm.

Leaf length on average is 10.2 cm, with a medium leaf width of 4.0 cm on average, and a large leaf ratio (2.55). There is no leaf blade or spine. The leaf has a straight shape in the cross section and an acute shape of apex. The leaf shape is elliptic (see descriptor 1 in section 7.2.9 of the *IPGRI Descriptors for Citrus*) and the margin type is wavy (see descriptor 4 in section 7.2.10 of the *IPGRI Descriptors for Citrus*). The base shape is absent (see descriptor 0 in section 7.2.12 of the *IPGRI Descriptors for Citrus*). The length of the petiole is medium, typically 10 mm, and wings are absent. Upper leaf surface color is typically dark green, RHS 139 A, while lower leave surface color is typically a strong yellowish green, RHS 144 C.

Fruiting, Fruit and Production Characteristics

'Mandarin Queen' mandarin fruit is typically harvested middle of January to end of April in Pilar de la Horadada, Alicante, Spain. Fruit production is similar to its parent, 'Satsuma'. Fruit production of a five year old 'Mandarin Queen' mandarin tree grafted in a plantation over Cleopatra rootstock is on average 75 kg per tree.

The 'Mandarin Queen' mandarin fruit has a short height, on average 45.2 mm, and a medium to large diameter, on average 65.9 mm. The color of the fruit surface is typically a vivid reddish orange, RHS 30A. It has a flattened general shape, absence of neck and presence of depression at stalk end. There are an intermediate number of radial grooves at the stock end, absent presence of collar, presence of depression at distal end, and complete grooved presence of the areola. There is no persistence of style. Occasionally there is the presence of a navel and, when present, the size of the navel is medium, while the bulging of the navel is intermediate to strong. The fruit rind has medium thickness, medium strength and medium oiliness, with a medium adherence to flesh, white color and loose density of albedo. The color of the albedo is typically white, RHS 155B and the presence of the albedo strand is medium present. The fruit surface texture is even (see descriptor 1 in section 7.4.12 of the *IPGRI Descriptors for Citrus*) and the pulp vesicles size is average. The date of maturity in Alicante, Spain is from the middle of January until the end of April.

The areola is grooved and the average diameter is from 5 mm to 15 mm. The average diameter of the stylar scar is from 5 mm to 15 mm and the protruding stylar point is large. The fruit has a strong glossy surface and the fruit's average weight is between 100 gr. to 150 gr. The size of the oil glands is typically 1 mm.

The fruit flesh has a medium orange color, large core diameter, and an average of 16 well developed segments. Specifically, the typical color of the mature internal fruit flesh is RHS 30D. The segment walls have a strong strength and there is an intermediate presence of a navel internally. There is no presence of rudimentary segments. The fruit, while virtually seedless, will occasionally have some seeds and the variety does not require pollination. Specifically, the number of seeds is absent or very few, the surface texture of the seeds is smooth and the average size of the seeds is 7 mm by 3 mm. The fruit flavor is sweet and lightly acidic, having a mandarin aroma, with soft pulp texture and thicker segment texture than a 'Clementine'. The fruit is also high in juiciness.

Results of storage trials have indicated that the first significant signs of fruit deterioration has been found at day 37, with no post harvesting treatments (as imazalil) at +5 Celsius. Fruit of the trial had a Brix of 13 and acid of 1.05%.

No susceptibilities to plant or fruit diseases or to pests beyond those normally associated with *citrus* species have been observed. Specifically, 'Mandarin Queen' mandarin is tolerant to *Citrus Tristeza Virus* (CTV) and *Alternaria* species. Further, aphids, mites and scales affect this variety similar to 'Clementines'. Like all varieties, only summer treatments for pests are needed.

DNA Analysis

DNA of Queen mandarin leaves was extracted using the Qiagen DNeasy Plant kit. Based on their level of polymorphism the following 32 simple sequence repeat (SSR) suitable markers were selected (see table). Extracted DNA was amplified by PCR and separated by capillary electrophoresis using a CEQ 8000 Beckman DNA analyser (Beckman). The table indicates the size of each of the two Mandarin Queen alleles of each marker. Therefore, the following primers can be used separately, or in combination, to identify 'Mandarin Queen' and to distinguish 'Mandarin Queen' from other varieties.

| Sequence forward (SEQ ID NO:) | Sequence reverse (SEQ ID NO:) | Allele 1 | Allele 2 |
|---|---|---|---|
| ATCACAATTACTAGC AGCGCC (1) | TTGCATTGTAGCATGT TGG (2) | 248 | 248 |
| GGACCACAACAAAGA CAG (3) | TGGAGACACAAAGAAG AA (4) | 132 | 146 |
| GCAAAACAAGCAGAC TACAAAT (5) | AGGACAGATGACCCAG ATGACA (6) | 203 | 205 |
| AAGCATTTAGGGAGG GTCACT (7) | TGCTGCTGCTGTTGTT GTTCT (8) | 216 | 226 |
| CAGCTCAACATGAAA GG (9) | TTGGAGAACAGGATGG (10) | 162 | 164 |
| AATGATGAGGGTAAA GATG (11) | ACCCATCACAAAACAG A (12) | 230 | 230 |
| CAATAAGAAAACGCA GG (13) | TGGTAGAGAAACAGAG GTG (14) | 122 | 124 |

-continued

| Sequence forward (SEQ ID NO:) | Sequence reverse (SEQ ID NO:) | Allele 1 | Allele 2 |
|---|---|---|---|
| CACCTTTCCCTTCCA (15) | TGAGGGACTAAACAGC A (16) | 261 | 265 |
| CAGAGACAGCCAAGA GA (17) | GCTTCTTACATTCCTC AAA (18) | 207 | 220 |
| CCACACAGGCAGACA (19) | CCTTGGAGGAGCTTTA C (20) | 198 | 227 |
| CCCAACAAACTCAAA CTTC (21) | TTTTTATTTCGGTCTC CTT (22) | 96 | 96 |
| CGGAACAACTAAAAC AAT (23) | TGGGCTTGTAGACAGT TA (24) | 104 | 107 |
| GACCCTGCCTCCAAA GTATC (25) | GTGGCTGTTGAGGGGT TG (26) | 241 | 249 |
| CCTTTTCACAGTTTG CTAT (27) | TCAATTCCTCTAGTGT GTGT (28) | 188 | 188 |
| TGTAGTCAAAAGCAT CAC (29) | TCTATGATTCCTGACT TTA (30) | 118 | 118 |
| TCCACAGATTGCCCA TTA (31) | CCCTAAAAACCAAGTG ACA (32) | 151 | 157 |
| GTTGCTGATGCTACA GATG (33) | CCTCTCTCTCTTCTTT ACCG(34) | 240 | 242 |
| CCTTATCTTCATCAC CTCCGTC (35) | TAAAAAGATGGGGCCT TGTG (36) | 237 | 239 |
| GCTGAGATGGGGATG AAAGA (37) | CCCCATCCTTTCAACT TGTG (38) | 176 | 176 |
| TCCCTATCATCGGCA ACTTC (39) | CAATAATGTTAGGCTG GATGGA (40) | 181 | 184 |
| TACCTCCACGTGTCA AACCA (41) | GCTGTCACGTTGGGTG TATG (42) | 141 | 147 |
| CGCGGATCATCTAGCA TACA (43) | CTTGGCACCATCAACA CATC (44) | 215 | 217 |
| CATTAAAATATCCGTG CCGC (45) | GAGCAAGTGCGTTGTT GTGT (46) | 226 | 226 |
| GAGCTCAAAACAATAG CCGC (47) | CATACCTCCCCGTCCA TCTA (48) | 332 | 343 |
| GAACCAGAATCAGAAC CCGA (49) | GGTGAGCATCTGGACG ACTT (50) | 215 | 215 |
| CACGCTCTTGACTTTC TCCC (51) | CTTTGCGTGTTTGTGC TGTT (52) | 156 | 165 |
| AGTCCGCCTTTGCTTT TTCT (53) | GGTGCAAAAGAGAGCG AGAG (54) | 135 | 145 |
| GAAAGGGTTACTTGAC CAGGC (55) | CTTCCCAGCTGCACAA GC (56) | 185 | 204 |

SEQUENCE LISTING

<160> NUMBER OF SEQ ID NOS: 56

<210> SEQ ID NO 1

-continued

<211> LENGTH: 21
<212> TYPE: DNA
<213> ORGANISM: Artificial Sequence
<220> FEATURE:
<223> OTHER INFORMATION: synthetic PCR amplification forward primer for
marker CAC23

<400> SEQUENCE: 1 atcacaatta ctagcagcgc c 21

<210> SEQ ID NO 2
<211> LENGTH: 19
<212> TYPE: DNA
<213> ORGANISM: Artificial Sequence
<220> FEATURE:
<223> OTHER INFORMATION: synthetic PCR amplification reverse primer for
marker CAC23

<400> SEQUENCE: 2 ttgcattgta gcatgttgg 19

<210> SEQ ID NO 3
<211> LENGTH: 18
<212> TYPE: DNA
<213> ORGANISM: Artificial Sequence
<220> FEATURE:
<223> OTHER INFORMATION: synthetic PCR amplification forward primer for
marker Ci01C06

<400> SEQUENCE: 3 ggaccacaac aaagacag 18

<210> SEQ ID NO 4
<211> LENGTH: 18
<212> TYPE: DNA
<213> ORGANISM: Artificial Sequence
<220> FEATURE:
<223> OTHER INFORMATION: synthetic PCR amplification reverse primer for
marker Ci01C06

<400> SEQUENCE: 4 tggagacaca aagaagaa 18

<210> SEQ ID NO 5
<211> LENGTH: 22
<212> TYPE: DNA
<213> ORGANISM: Artificial Sequence
<220> FEATURE:
<223> OTHER INFORMATION: synthetic PCR amplification forward primer for
marker Ci01D11

<400> SEQUENCE: 5 gcaaaacaag cagactacaa at 22

<210> SEQ ID NO 6
<211> LENGTH: 22
<212> TYPE: DNA
<213> ORGANISM: Artificial Sequence
<220> FEATURE:
<223> OTHER INFORMATION: synthetic PCR amplification reverse primer for
marker Ci01D11

<400> SEQUENCE: 6 aggacagatg acccagatga ca 22

<210> SEQ ID NO 7

-continued

<211> LENGTH: 21
<212> TYPE: DNA
<213> ORGANISM: Artificial Sequence
<220> FEATURE:
<223> OTHER INFORMATION: synthetic PCR amplification forward primer for
marker Ci01F04a

<400> SEQUENCE: 7 aagcatttag ggagggtcac t 21

<210> SEQ ID NO 8
<211> LENGTH: 21
<212> TYPE: DNA
<213> ORGANISM: Artificial Sequence
<220> FEATURE:
<223> OTHER INFORMATION: synthetic PCR amplification reverse primer for
marker Ci01F04a

<400> SEQUENCE: 8 tgctgctgct gttgttgttc t 21

<210> SEQ ID NO 9
<211> LENGTH: 17
<212> TYPE: DNA
<213> ORGANISM: Artificial Sequence
<220> FEATURE:
<223> OTHER INFORMATION: synthetic PCR amplification forward primer for
marker Ci02B07

<400> SEQUENCE: 9 cagctcaaca tgaaagg 17

<210> SEQ ID NO 10
<211> LENGTH: 16
<212> TYPE: DNA
<213> ORGANISM: Artificial Sequence
<220> FEATURE:
<223> OTHER INFORMATION: synthetic PCR amplification reverse primer for
marker Ci02B07

<400> SEQUENCE: 10 ttggagaaca ggatgg 16

<210> SEQ ID NO 11
<211> LENGTH: 19
<212> TYPE: DNA
<213> ORGANISM: Artificial Sequence
<220> FEATURE:
<223> OTHER INFORMATION: synthetic PCR amplification forward primer for
marker Ci02D09

<400> SEQUENCE: 11 aatgatgagg gtaaagatg 19

<210> SEQ ID NO 12
<211> LENGTH: 17
<212> TYPE: DNA
<213> ORGANISM: Artificial Sequence
<220> FEATURE:
<223> OTHER INFORMATION: synthetic PCR amplification reverse primer for
marker Ci02D09

<400> SEQUENCE: 12 acccatcaca aaacaga 17

<210> SEQ ID NO 13

-continued

<211> LENGTH: 17
<212> TYPE: DNA
<213> ORGANISM: Artificial Sequence
<220> FEATURE:
<223> OTHER INFORMATION: synthetic PCR amplification forward primer for
marker Ci02G02

<400> SEQUENCE: 13 caataagaaa acgcagg 17

<210> SEQ ID NO 14
<211> LENGTH: 19
<212> TYPE: DNA
<213> ORGANISM: Artificial Sequence
<220> FEATURE:
<223> OTHER INFORMATION: synthetic PCR amplification reverse primer for
marker Ci02G02

<400> SEQUENCE: 14 tggtagagaa acagaggtg 19

<210> SEQ ID NO 15
<211> LENGTH: 15
<212> TYPE: DNA
<213> ORGANISM: Artificial Sequence
<220> FEATURE:
<223> OTHER INFORMATION: synthetic PCR amplification forward primer for
marker Ci03B07

<400> SEQUENCE: 15 cacctttccc ttcca 15

<210> SEQ ID NO 16
<211> LENGTH: 17
<212> TYPE: DNA
<213> ORGANISM: Artificial Sequence
<220> FEATURE:
<223> OTHER INFORMATION: synthetic PCR amplification reverse primer for
marker Ci03B07

<400> SEQUENCE: 16 tgagggacta aacagca 17

<210> SEQ ID NO 17
<211> LENGTH: 17
<212> TYPE: DNA
<213> ORGANISM: Artificial Sequence
<220> FEATURE:
<223> OTHER INFORMATION: synthetic PCR amplification forward primer for
marker Ci03C08

<400> SEQUENCE: 17 cagagacagc caagaga 17

<210> SEQ ID NO 18
<211> LENGTH: 19
<212> TYPE: DNA
<213> ORGANISM: Artificial Sequence
<220> FEATURE:
<223> OTHER INFORMATION: synthetic PCR amplification reverse primer for
marker Ci03C08

<400> SEQUENCE: 18 gcttcttaca ttcctcaaa 19

<210> SEQ ID NO 19

-continued

<211> LENGTH: 15
<212> TYPE: DNA
<213> ORGANISM: Artificial Sequence
<220> FEATURE:
<223> OTHER INFORMATION: synthetic PCR amplification forward primer for
marker Ci03G05

<400> SEQUENCE: 19 ccacacaggc agaca 15

<210> SEQ ID NO 20
<211> LENGTH: 17
<212> TYPE: DNA
<213> ORGANISM: Artificial Sequence
<220> FEATURE:
<223> OTHER INFORMATION: synthetic PCR amplification reverse primer for
marker Ci03G05

<400> SEQUENCE: 20 ccttggagga gctttac 17

<210> SEQ ID NO 21
<211> LENGTH: 19
<212> TYPE: DNA
<213> ORGANISM: Artificial Sequence
<220> FEATURE:
<223> OTHER INFORMATION: synthetic PCR amplification forward primer for
marker Ci06A12

<400> SEQUENCE: 21 cccaacaaac tcaaacttc 19

<210> SEQ ID NO 22
<211> LENGTH: 19
<212> TYPE: DNA
<213> ORGANISM: Artificial Sequence
<220> FEATURE:
<223> OTHER INFORMATION: synthetic PCR amplification reverse primer for
marker Ci06A12

<400> SEQUENCE: 22 tttttatttc ggtctcctt 19

<210> SEQ ID NO 23
<211> LENGTH: 18
<212> TYPE: DNA
<213> ORGANISM: Artificial Sequence
<220> FEATURE:
<223> OTHER INFORMATION: synthetic PCR amplification forward primer for
marker Ci06B07

<400> SEQUENCE: 23 cggaacaact aaaacaat 18

<210> SEQ ID NO 24
<211> LENGTH: 18
<212> TYPE: DNA
<213> ORGANISM: Artificial Sequence
<220> FEATURE:
<223> OTHER INFORMATION: synthetic PCR amplification reverse primer for
marker Ci06B07

<400> SEQUENCE: 24 tgggcttgta gacagtta 18

<210> SEQ ID NO 25

-continued

<211> LENGTH: 20
<212> TYPE: DNA
<213> ORGANISM: Artificial Sequence
<220> FEATURE:
<223> OTHER INFORMATION: synthetic PCR amplification forward primer for
marker Ci07C09

<400> SEQUENCE: 25 gaccctgcct ccaaagtatc 20

<210> SEQ ID NO 26
<211> LENGTH: 18
<212> TYPE: DNA
<213> ORGANISM: Artificial Sequence
<220> FEATURE:
<223> OTHER INFORMATION: synthetic PCR amplification reverse primer for
marker Ci0709

<400> SEQUENCE: 26 gtggctgttg aggggttg 18

<210> SEQ ID NO 27
<211> LENGTH: 19
<212> TYPE: DNA
<213> ORGANISM: Artificial Sequence
<220> FEATURE:
<223> OTHER INFORMATION: synthetic PCR amplification forward primer for
marker Ci0D06

<400> SEQUENCE: 27 ccttttcaca gtttgctat 19

<210> SEQ ID NO 28
<211> LENGTH: 20
<212> TYPE: DNA
<213> ORGANISM: Artificial Sequence
<220> FEATURE:
<223> OTHER INFORMATION: synthetic PCR amplification reverse primer for
marker Ci07D06

<400> SEQUENCE: 28 tcaattcctc tagtgtgtgt 20

<210> SEQ ID NO 29
<211> LENGTH: 18
<212> TYPE: DNA
<213> ORGANISM: Artificial Sequence
<220> FEATURE:
<223> OTHER INFORMATION: synthetic PCR amplification forward primer for
marker Ci07E12

<400> SEQUENCE: 29 tgtagtcaaa agcatcac 18

<210> SEQ ID NO 30
<211> LENGTH: 19
<212> TYPE: DNA
<213> ORGANISM: Artificial Sequence
<220> FEATURE:
<223> OTHER INFORMATION: synthetic PCR amplification reverse primer for
marker Ci07E12

<400> SEQUENCE: 30 tctatgattc ctgacttta 19

<210> SEQ ID NO 31

-continued

<211> LENGTH: 18
<212> TYPE: DNA
<213> ORGANISM: Artificial Sequence
<220> FEATURE:
<223> OTHER INFORMATION: synthetic PCR amplification forward primer for
marker Ci08C05

<400> SEQUENCE: 31 tccacagatt gcccatta 18

<210> SEQ ID NO 32
<211> LENGTH: 19
<212> TYPE: DNA
<213> ORGANISM: Artificial Sequence
<220> FEATURE:
<223> OTHER INFORMATION: synthetic PCR amplification reverse primer for
marker Ci08C05

<400> SEQUENCE: 32 ccctaaaaac caagtgaca 19

<210> SEQ ID NO 33
<211> LENGTH: 19
<212> TYPE: DNA
<213> ORGANISM: Artificial Sequence
<220> FEATURE:
<223> OTHER INFORMATION: synthetic PCR amplification forward primer for
marker IDCAX

<400> SEQUENCE: 33 gttgctgatg ctacagatg 19

<210> SEQ ID NO 34
<211> LENGTH: 20
<212> TYPE: DNA
<213> ORGANISM: Artificial Sequence
<220> FEATURE:
<223> OTHER INFORMATION: synthetic PCR amplification reverse primer for
marker IDCAX

<400> SEQUENCE: 34 cctctctctc ttctttaccg 20

<210> SEQ ID NO 35
<211> LENGTH: 22
<212> TYPE: DNA
<213> ORGANISM: Artificial Sequence
<220> FEATURE:
<223> OTHER INFORMATION: synthetic PCR amplification forward primer for
marker MEST104

<400> SEQUENCE: 35 ccttatcttc atcacctccg tc 22

<210> SEQ ID NO 36
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST104

<400> SEQUENCE: 36 taaaaagatg gggccttgtg 20

<210> SEQ ID NO 37

-continued

<211> LENGTH: 20
<212> TYPE: DNA
<213> ORGANISM: Artificial Sequence
<220> FEATURE:
<223> OTHER INFORMATION: synthetic PCR amplification forward primer for
marker MEST107

<400> SEQUENCE: 37 gctgagatgg ggatgaaaga 20

<210> SEQ ID NO 38
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST107

<400> SEQUENCE: 38 ccccatcctt tcaacttgtg 20

<210> SEQ ID NO 39
<211> LENGTH: 20
<212> TYPE: DNA
<213> ORGANISM: Artificial Sequence
<220> FEATURE:
<223> OTHER INFORMATION: synthetic PCR amplification forward primer for
marker MEST121

<400> SEQUENCE: 39 tccctatcat cggcaacttc 20

<210> SEQ ID NO 40
<211> LENGTH: 22
<212> TYPE: DNA
<213> ORGANISM: Artificial Sequence
<220> FEATURE:
<223> OTHER INFORMATION: synthetic PCR amplification reverse primer for
marker MEST121

<400> SEQUENCE: 40 caataatgtt aggctggatg ga 22

<210> SEQ ID NO 41
<211> LENGTH: 20
<212> TYPE: DNA
<213> ORGANISM: Artificial Sequence
<220> FEATURE:
<223> OTHER INFORMATION: synthetic PCR amplification forward primer for
marker MEST131

<400> SEQUENCE: 41 tacctccacg tgtcaaacca 20

<210> SEQ ID NO 42
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST131

<400> SEQUENCE: 42 gctgtcacgt tgggtgtatg 20

<210> SEQ ID NO 43

-continued

<211> LENGTH: 20
<212> TYPE: DNA
<213> ORGANISM: Artificial Sequence
<220> FEATURE:
<223> OTHER INFORMATION: synthetic PCR amplification forward primer for
marker MEST192

<400> SEQUENCE: 43 cgcggatcat ctagcataca 20

<210> SEQ ID NO 44
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST192

<400> SEQUENCE: 44 cttggcacca tcaacacatc 20

<210> SEQ ID NO 45
<211> LENGTH: 20
<212> TYPE: DNA
<213> ORGANISM: Artificial Sequence
<220> FEATURE:
<223> OTHER INFORMATION: synthetic PCR amplification forward primer for
marker MEST256

<400> SEQUENCE: 45 cattaaaata tccgtgccgc 20

<210> SEQ ID NO 46
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST256

<400> SEQUENCE: 46 gagcaagtgc gttgttgtgt 20

<210> SEQ ID NO 47
<211> LENGTH: 20
<212> TYPE: DNA
<213> ORGANISM: Artificial Sequence
<220> FEATURE:
<223> OTHER INFORMATION: synthetic PCR amplification forward primer for
marker MEST431

<400> SEQUENCE: 47 gagctcaaaa caatagccgc 20

<210> SEQ ID NO 48
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST431

<400> SEQUENCE: 48 catacctccc cgtccatcta 20

<210> SEQ ID NO 49

-continued

<211> LENGTH: 20
<212> TYPE: DNA
<213> ORGANISM: Artificial Sequence
<220> FEATURE:
<223> OTHER INFORMATION: synthetic PCR amplification forward primer for
marker MEST46

<400> SEQUENCE: 49 gaaccagaat cagaacccga 20

<210> SEQ ID NO 50
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST46

<400> SEQUENCE: 50 ggtgagcatc tggacgactt 20

<210> SEQ ID NO 51
<211> LENGTH: 20
<212> TYPE: DNA
<213> ORGANISM: Artificial Sequence
<220> FEATURE:
<223> OTHER INFORMATION: synthetic PCR amplification forward primer for
marker MEST488

<400> SEQUENCE: 51 cacgctcttg actttctccc 20

<210> SEQ ID NO 52
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST488

<400> SEQUENCE: 52 ctttgcgtgt ttgtgctgtt 20

<210> SEQ ID NO 53
<211> LENGTH: 20
<212> TYPE: DNA
<213> ORGANISM: Artificial Sequence
<220> FEATURE:
<223> OTHER INFORMATION: synthetic PCR amplification forward primer for
marker MEST56

<400> SEQUENCE: 53 agtccgcctt tgctttttct 20

<210> SEQ ID NO 54
<211> LENGTH: 20
<212> TYPE: DNA
<213> ORGANISM: Artificial Sequence
<220> FEATURE:
<223> OTHER INFORMATION: synthetic PCR amplification reverse primer for
marker MEST56

<400> SEQUENCE: 54 ggtgcaaaag agagcgagag 20

<210> SEQ ID NO 55

-continued

```
<211> LENGTH: 21
<212> TYPE: DNA
<213> ORGANISM: Artificial Sequence
<220> FEATURE:
<223> OTHER INFORMATION: synthetic PCR amplification forward primer for
      marker TAA15

<400> SEQUENCE: 55

gaaagggtta cttgaccagg c                                              21


<210> SEQ ID NO 56
<211> LENGTH: 18
<212> TYPE: DNA
<213> ORGANISM: Artificial Sequence
<220> FEATURE:
<223> OTHER INFORMATION: synthetic PCR amplification reverse primer for
      marker TAA15

<400> SEQUENCE: 56

cttcccagct gcacaagc                                                  18
```

What is claimed is:

1. A new and distinct cultivar of mandarin tree having the characteristics substantially as described and illustrated herein.

* * * * *